US012241776B2

(12) United States Patent
Rozental et al.

(10) Patent No.: US 12,241,776 B2
(45) Date of Patent: *Mar. 4, 2025

(54) ULTRASOUND DETECTION BASED ON PHASE SHIFT

(71) Applicant: TECHNION RESEARCH & DEVELOPMENT FOUNDATION LIMITED, Haifa (IL)

(72) Inventors: Amir Rozental, Haifa (IL); Lucas Riobo, Buenos Aires (AR); Yoav Hazan, Haifa (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/370,040

(22) Filed: Sep. 19, 2023

(65) Prior Publication Data

US 2024/0011822 A1 Jan. 11, 2024

Related U.S. Application Data

(63) Continuation of application No. 17/420,903, filed as application No. PCT/IL2020/050016 on Jan. 7, 2020, now Pat. No. 11,796,383.

(60) Provisional application No. 62/833,912, filed on Apr. 15, 2019, provisional application No. 62/789,015, filed on Jan. 7, 2019.

(51) Int. Cl.
*G01H 9/00* (2006.01)
*A61B 5/00* (2006.01)

(52) U.S. Cl.
CPC ............ *G01H 9/004* (2013.01); *A61B 5/0097* (2013.01)

(58) Field of Classification Search
None
See application file for complete search history.

(56) References Cited

U.S. PATENT DOCUMENTS

| | | | | |
|---|---|---|---|---|
| 4,977,546 A | * | 12/1990 | Flatley | G01H 9/004 367/149 |
| 11,796,383 B2 | * | 10/2023 | Rozental | G01H 9/004 |

(Continued)

FOREIGN PATENT DOCUMENTS

| | | |
|---|---|---|
| EP | 3841361 A1 | 6/2021 |
| WO | 2020039436 A1 | 2/2020 |

OTHER PUBLICATIONS

Lucas Riobó, Yoav Hazan, Francisco Veiras, María Garea, Patricio Sorichetti, and Amir Rosenthal, "Noise reduction in resonator-based ultrasound sensors by using a CW laser and phase detection," Opt. Lett. 44, 2677-2680 (2019). https://doi.org/10.1364/OL.44.002677.

(Continued)

*Primary Examiner* — John E Breene
(74) *Attorney, Agent, or Firm* — The Roy Gross Law Firm, LLC; Roy Gross

(57) ABSTRACT

A system and method of detecting acoustic waves including directing a continuous-wave source laser beam to an optical resonator that is impinged by acoustic the waves. Optionally, the source laser beam can propagate through the optical resonator, thereby generating a propagated laser beam. Using an interferometer, the acoustic waves can be detected by monitoring transients in an optical phase of the propagated laser beam.

19 Claims, 7 Drawing Sheets

(56) References Cited

U.S. PATENT DOCUMENTS

| | | | |
|---|---|---|---|
| 2014/0114187 A1* | 4/2014 | Rozental | A61B 8/44 600/407 |
| 2018/0238833 A1* | 8/2018 | Somekh | G01N 29/036 |
| 2019/0049412 A1* | 2/2019 | Cranch | G01N 29/12 |

OTHER PUBLICATIONS

Wissmeyer, G., Pleitez, M.A., Rosenthal, A. et al. Looking at sound: optoacoustics with all-optical ultrasound detection. Light Sci Appl 7, 53 (2018). https://doi.org/10.1038/s41377-018-0036-7.

Gatti D, Galzerano G, Janner D, Longhi S, Laporta P. Fiber strain sensor based on a pi-phase-shifted Bragg grating and the Pound-Drever-Hall technique. Opt Express. Feb. 4, 2008;16(3):1945-50. doi: 10.1364/oe.16.001945. PMID: 18542273.

L. Hu and M. Han, "Reduction of Laser Frequency Noise and Intensity Noise in Phase-Shifted Fiber Bragg Grating Acoustic-Emission Sensor System," in IEEE Sensors Journal, vol. 17, No. 15, pp. 4820-4825, 1 Aug. 1, 2017, doi: 10.1109/JSEN.2017.2716410.

Rosenthal A, Razansky D, Ntziachristos V. High-sensitivity compact ultrasonic detector based on a pi-phase-shifted fiber Bragg grating. Opt Lett. May 15, 2011;36(10):1833-5. doi: 10.1364/OL.36.001833. PMID: 21593906.

M. R. Salehi and B. Cabon, "Theoretical and experimental analysis of influence of phase-to-intensity noise conversion in interferometric systems," in Journal of Lightwave Technology, vol. 22, No. 6, pp. 1510-1518, Jun. 2004, doi: 10.1109/JLT.2004.829220.

T. Erdogan, "Fiber grating spectra," in Journal of Lightwave Technology, vol. 15, No. 8, pp. 1277-1294, Aug. 1997, doi: 10.1109/50.618322.

Rosenthal, A., Razansky, D., & Ntziachristos, V. (2012). Wideband optical sensing using pulse interferometry. Optics express, 20(17), 19016-19029.

B. Dong, C. Sun and H. F. Zhang, "Optical Detection of Ultrasound in Photoacoustic Imaging," in IEEE Transactions on Biomedical Engineering, vol. 64, No. 1, pp. 4-15, Jan. 2017, doi: 10.1109/TBME.2016.2605451.

Shnaiderman, R., Wissmeyer, G., Seeger, M., Soliman, D., Estrada, H., Razansky, D., Rosenthal, A., & Ntziachristos, V. (2017). "Fiber interferometer for hybrid optical and optoacoustic intravital microscopy". Optica, 4(10), 1180-1187.

Chen, S. L., Guo, L. J., & Wang, X. (2015). "All-optical photoacoustic microscopy". Photoacoustics, 3(4), 143-150. https://doi.org/10.1016/j.pacs.2015.11.001.

J. Guo and C. Yang, "Highly Stabilized Phase-Shifted Fiber Bragg Grating Sensing System for Ultrasonic Detection," in IEEE Photonics Technology Letters, vol. 27, No. 8, pp. 848-851, 15 Apr. 15, 2015, doi: 10.1109/LPT.2015.2396530.

C. Chao, S. Ashkenazi, S. Huang, M. O'Donnell and L. J. Guo, "High-frequency ultrasound sensors using polymer microring resonators," in IEEE Transactions on Ultrasonics, Ferroelectrics, and Frequency Control, vol. 54, No. 5, pp. 957-965, May 2007, doi: 10.1109/TUFFC.2007.341.

Rosenthal, A., Omar, M., Estrada, H., Kellnberger, S., Razansky, D., & Ntziachristos, V. (2014). "Embedded ultrasound sensor in a silicon-on-insulator photonic platform". Applied Physics Letters, 104(2), Feb. 11, 2016. doi: 10.1063/1.4860983.

C. Zhang, S.-L. Chen, T. Ling and L. J. Guo, "Review of Imprinted Polymer Microrings as Ultrasound Detectors: Design, Fabrication, and Characterization," in IEEE Sensors Journal, vol. 15, No. 6, pp. 3241-3248, Jun. 2015, doi: 10.1109/JSEN.2015.2421519.

R. Nuster, H. Gruen, B. Reitinger, P. Burgholzer, S. Gratt, K. Passler, and G. Paltauf, "Downstream Fabry-Perot interferometer for acoustic wave monitoring in photoacoustic tomography," Opt. Lett. 36, 981-983 (2011).

Hajireza P, Krause K, Brett M, Zemp R. "Glancing angle deposited nanostructured film Fabry-Perot etalons for optical detection of ultrasound". Opt Express. Mar. 11, 2013;21(5):6391-400. doi: 10.1364/OE.21.006391. PMID: 23482209.

Morris, P., Hurrell, A., Shaw, A., Zhang, E., & Beard, P. (2009). A Fabry-Pérot fiber-optic ultrasonic hydrophone for the simultaneous measurement of temperature and acoustic pressure. The Journal of the Acoustical Society of America, 125(6), 3611-3622.

T. Ling, S. Chen, and L. J. Guo, "Fabrication and characterization of High Q polymer micro-ring resonator and its application as a sensitive ultrasonic detector," Opt. Express 19, 861-869 (2011).

Huang, S. W., Hou, Y., Ashkenazi, S., & O'Donnell, M. (2008). "High-resolution ultrasonic imaging using an etalon detector array". Applied physics letters, 93(11), 113501.

Guggenheim, J.A., Li, J., Allen, T.J. et al. "Ultrasensitive plano-concave optical microresonators for ultrasound sensing". Nature Photon 11, 714-719 (2017). https://doi.org/10.1038/s41566-017-0027-x.

Rosenthal, A., Kellnberger, S., Bozhko, D., Chekkoury, A., Omar, M., Razansky, D., & Ntziachristos, V. (2014). "Sensitive interferometric detection of ultrasound for minimally invasive clinical imaging applications". Laser & Photonics Reviews, 8(3), 450-457.

Volodarsky O, Hazan Y, Rosenthal A. "Ultrasound detection via low-noise pulse interferometry using a free-space Fabry-Pérot". Opt Express. Aug. 20, 2018;26(17):22405-22418. doi: 10.1364/OE.26.022405. PMID: 30130935.

D. Liu, Y. Liang, L. Jin, H. Sun, L. Cheng, and B. Guan, "Highly sensitive fiber laser ultrasound hydrophones for sensing and imaging applications," Opt. Lett. 41, 4530-4533 (2016). http://dx.doi.org/10.1364/OL.41.004530.

Liang, Y., Jin, L., Wang, L. et al. "Fiber-Laser-Based Ultrasound Sensor for Photoacoustic Imaging". Sci Rep 7, 40849 (2017). https://doi.org/10.1038/srep40849.

Hazan Y, Rosenthal A. "Passive-demodulation pulse interferometry for ultrasound detection with a high dynamic range". Opt Lett. Mar. 1, 2018;43(5):1039-1042. doi: 10.1364/OL.43.001039. PMID: 29489775.

PCT International Search Report for International Application No. PCT/IL2020/050016, mailed Apr. 23, 2020, 4pp.

PCT Written Opinion for International Application No. PCT/IL2020/050016, mailed Apr. 23, 2020, 5pp.

PCT International Preliminary Report on Patentability for International Application No. PCT/IL2020/050016, issued Jun. 16, 2021, 6pp.

* cited by examiner

ULTRASOUND DETECTION BASED ON PHASE SHIFT

CROSS-REFERENCE TO RELATED APPLICATIONS

This application is a Continuation of U.S. patent application Ser. No. 17/420,903, filed Jul. 6, 2021, which is a National Phase of PCT Patent Application No. PCT/IL2020/050016 having International filing date of Jan. 7, 2020, which claims the benefit of priority of U.S. Provisional Patent Application Nos. 62/789,015, filed Jan. 7, 2019, and 62/833,912, filed Apr. 15, 2019, the contents of which are all incorporated herein by reference in their entirety.

BACKGROUND

The invention relates to the field of ultrasound detection.

In the last decade, there has been an increasing interest in optical techniques for ultrasound detection, as an alternative to piezoelectric devices, e.g., in biomedical applications. One of the common optical approaches for ultrasound detection is the use of optical resonators, which can trap light within small volumes and thus facilitate detector miniaturization without loss of sensitivity. When an acoustic wave impinges on an optical resonator, it perturbs its refractive index and deforms its structure, resulting in a modulation of the resonance wavelength. By monitoring the shifts in the resonance wavelength, one can effectively measure the ultrasound-induced pressure within the resonator. Despite the simplicity of this method, the maximum achievable signal-to-noise ratio is limited by the laser phase and intensity noise.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provide, in an embodiment, a system comprising an optical resonator configured to be impinged by acoustic waves; a continuous-wave source laser beam directed to said optical resonator, wherein said source laser beam is propagated through said optical resonator, thereby generating a propagated laser beam; and an interferometer configured for detecting a signal associated with said acoustic wave by monitoring transients in the optical phase in said propagated laser beam, wherein said transients are indicative of a waveform of said acoustic wave.

There is also provided, in an embodiment, a method comprising: directing a continuous-wave source laser beam to an optical resonator that is impinged by acoustic waves, wherein said source laser beam is propagated through said optical resonator, thereby generating a propagated laser beam; and detecting a signal associated with said acoustic waves by monitoring, using an interferometer, transients in the optical phase in said propagated laser beam, wherein said transients are indicative of a waveform of said acoustic wave.

In some embodiments, said monitoring comprises interfering said propagated laser beam with a reference beam.

In some embodiments, said reference beam comprises a replica of said source laser beam. In some embodiments, said propagated laser beam and said reference laser beam have an optical path difference equal to zero at a wavelength of said source laser beam.

In some embodiments, said reference beam comprises a time-delayed version of said propagated laser beam.

In some embodiments, said optical resonator is selected from the group consisting of: π phase-shifted Bragg grating (π-BG), Fabry-Perot cavity, and optical-ring resonator.

In some embodiments, said laser beam is tuned to a center of a transmission notch of said optical resonator.

In some embodiments, said interferometer is a Mach-Zehnder interferometer (MZI).

In some embodiments, said monitoring further comprises measuring an optical power transmission in said propagated laser beam and said reference laser beam, wherein said optical power transmission is indicative of said transients.

In some embodiments, said measuring of said optical power transmission is performed by at least one balanced photo-detector.

In some embodiments, said acoustic waves are ultrasound acoustic waves.

In some embodiments, said ultrasound acoustic waves are generated opto-acoustically via the transformation of a modulated optical beam into acoustic waves.

In some embodiments, said modulated optical beam comprises optical pulses.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1B:
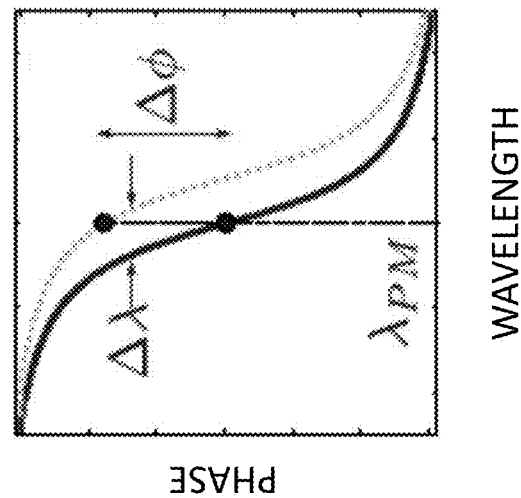
FIGS. 1A-1B illustrate an intensity resonator response function and a phase resonator response function.

Disclosed herein are a system and method for ultrasound detection, based on monitoring variations in the phase of a continuous-wave (CW) laser beam applied to an optical detection device, which is subjected to ultrasound acoustic waves.

In some embodiments, the optical detection device comprises an optical resonator, wherein the ultrasound acoustic waves cause a modulation of a refractive index of the optical resonator, and wherein the modulation is correlated with a waveform of the ultrasound.

In some embodiments, an interrogation and/or detection light source, e.g., a continuous wave (CW) laser beam, is directed at the optical resonator, wherein the optical resonator causes a modulation of the detection light source which is correlated with the changes in the refractive index of the optical resonator.

In some embodiments, the optical detection device comprises an interferometer which measures interference patterns between the detection light source and, e.g., a reference light beam.

In some embodiments, the measurement comprises measuring a phase shift between the sample and reference light sources, wherein the phase shift is indicative of a waveform of the ultrasound waves.

In some embodiments, the present system provides for an improvement in detection sensitivity over current ultrasound detectors, based, at least in part, on improvement in the signal-to-noise (SNR) ratio.

In some embodiments, the present system provides for an ultrasound detection method using passive high-Q optical resonators, based on a balanced phase detection method that can significantly reduce the effect of the laser phase noise on the measurement, while maintaining the gain in signal due to the high Q of the resonator. In some embodiments, an exemplary system as described herein below may be capable of a 24-fold increase in SNR compared to intensity-based methods, with shot-noise-limited detection for powers up to 1 mW.

For example, ultrasound detectors based on measuring an intensity of a detection light source (e.g., a laser beam) at the output of an optical resonator, suffer from two potential noise sources: Photodetector noise, and laser frequency noise. Photodetector noise can be offset at least partially by, e.g., using higher laser powers or resonators with higher Q-factors. However, for sufficiently high powers and Q-factors, the laser frequency noise becomes the dominant noise factor, for which sensitivity cannot be further improved via higher Q factors or laser powers. In this case, the optical SNR can be improved only by reducing the frequency noise of the laser, i.e. using interrogation lasers with narrower linewidths, leading to a higher system cost.

Other methods for improving SNR include, e.g., adding a second, static resonator during the ultrasound measurement and effectively subtracting the noise signal from the ultrasound signal, or via coherence-restored pulse interferometry (CRPI). However, these approaches carry a cost of a more complex optical system, that may also require post-processing of the signals.

A potential advantage of the present system is, therefore, in that it provides for a significantly reduced frequency noise compared to intensity-based detection system, without adding to the complexity and cost of existing detection systems. In addition, the present system is generally compatible with any passive optical resonator.

The transmission spectrum of many optical resonators, as a function of wavelength, may be described as follows:

$$t(k) = \frac{\alpha}{\alpha - i\Delta k} \quad (1)$$

where $\alpha$ is a constant and $\Delta k$ is the wavenumber detuning, given by:

$$\Delta k = -2\pi n_0 \left( \frac{1}{\lambda} - \frac{1}{\lambda_0} \right). \quad (2)$$

Here, $n_0$ is the refractive index of the fiber, $\lambda$ is the optical wavelength, and $\lambda_0$ is the central wavelength of the grating.

The power transmission $T(\Delta k)$ and phase $\phi(\Delta k)$ corresponding to $t(\Delta k)$ are respectively given by $$|t(\Delta k)|^2 = \frac{\alpha^2}{\alpha^2 + \Delta k^2}, \quad (3)$$

$$phi(\Delta k) = \arctan \frac{\alpha}{\Delta k}.$$

The power transmission $T(\Delta k)$ has a Lorentzian shape with a full-width at half maximum (FWHM) of $2\alpha$, yielding a Q factor given by $Q = \frac{1}{2}\lambda_0$.

When ultrasound detection is performed via intensity-based methods, the laser source is often tuned to the steepest slope of $T(\Delta k)$, obtained at $\Delta k = \pm \alpha/3$ and equal to $\mp 0.54\alpha^{-1}$. Accordingly, when the resonance shifts by $\delta k$, the resulting change in the monitored power transmission is $\delta T = \mp 0.54\alpha^{-1}\delta k$. Because $\delta T$ is inversely proportional to $\alpha$, and thus to the Q factor, the sensitivity obtained via intensity-based methods is often optimized by using resonators with high Q factors. However, not only the maximum slope of $T(k)$ is inversely proportional to a, but also the maximum slope of $\phi(\Delta k)$, which is obtained at $\Delta k = 0$ and is equal to $-\alpha^{-1}$. Thus, the gain in signal obtained in intensity-based measurements using high-Q resonators may also be obtained in the present, phase-based, system.

Figure 1A:
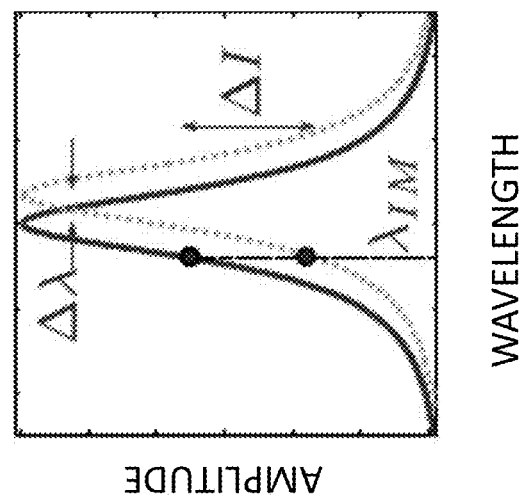

FIGS. 1A-1B illustrate an intensity resonator response function (FIG. 1A) and a phase resonator response function (FIG. 1B), wherein the dashed lines represent the spectrum shift caused by ultrasound excitation. In some embodiments, and as shown in FIGS. 1A and 1B, When the resonator interacts with the acoustic wave, stress and strain are generated within the structure, which produces a shift of the optical spectrum.

Figure 2A:
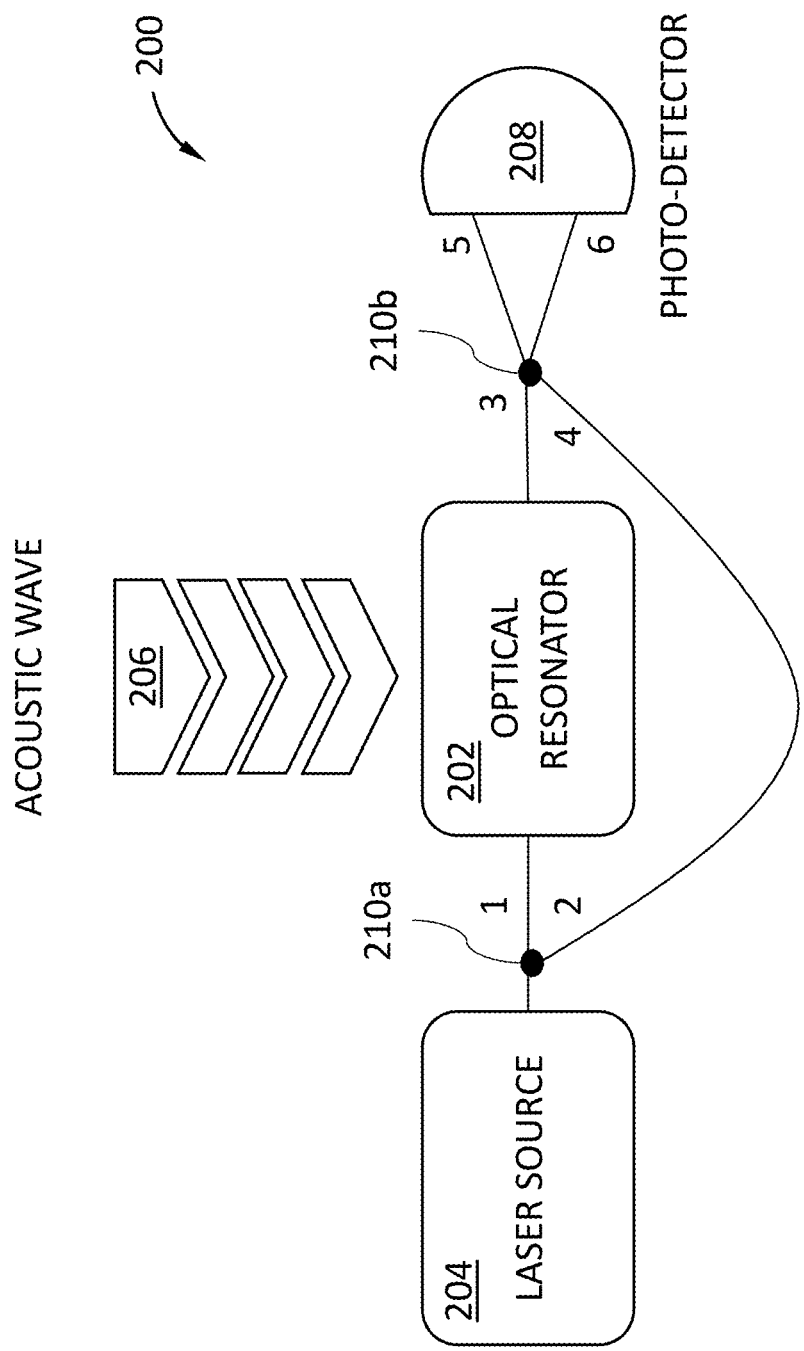
FIGS. 2A-2B schematically illustrate exemplary systems for ultrasound detection, in accordance with some embodiments.
Figure 2B:
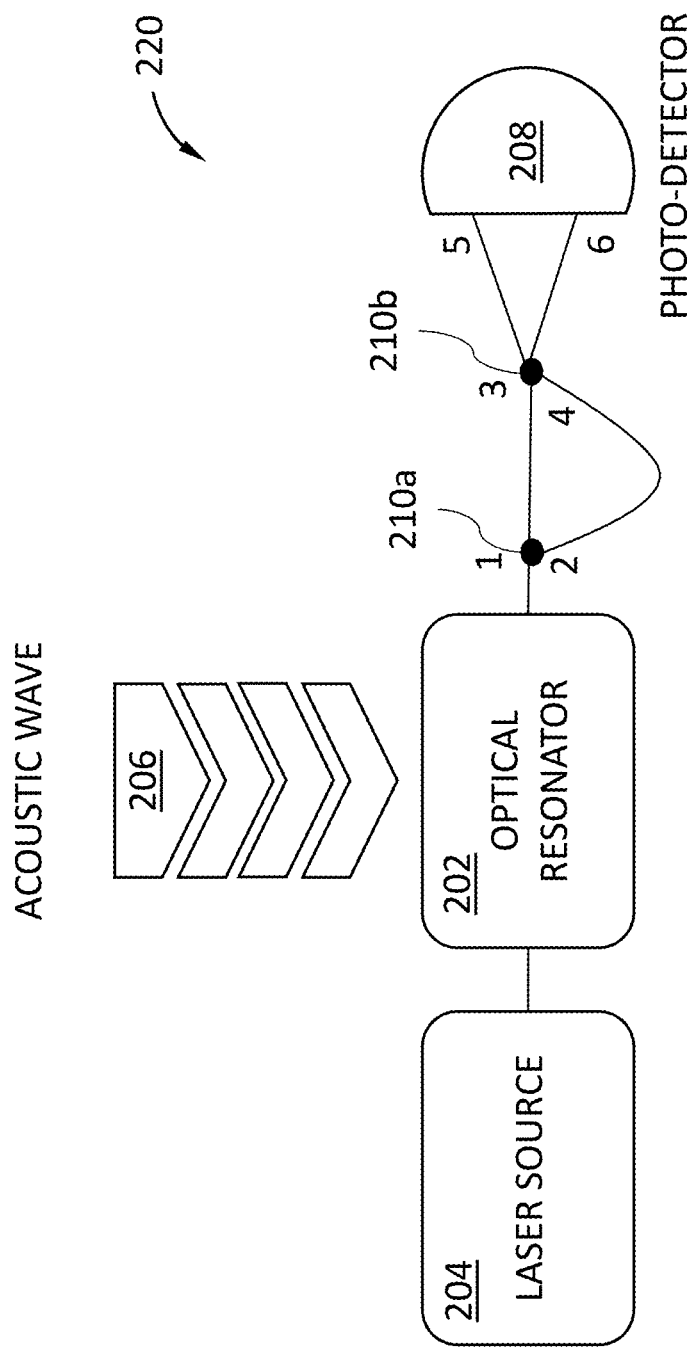

FIGS. 2A-2B schematically illustrate exemplary systems 200 and 220 for ultrasound detection, in accordance with some embodiments.

In some embodiments, system 200 in FIG. 2A comprises, e.g., an optical resonator 202. In some embodiments, exemplary optical resonator 202 may comprise, e.g., a π phase-shifted fiber-Bragg grating (π-FBG) with a resonance of $\lambda_B = 1549.11$ nm, and a FWHM of approximately 2 pm. In some embodiments, the FWHM is approximately 0.5 GHz. In some embodiments, the optical resonator may comprise any passive optical resonator, such as a Fabry-Perot cavity, and optical ring or micro-ring resonators. In some embodiments, additional and/or other types of optical resonators may be used. In some embodiments, an optical resonator of system 200 may be fabricated in silicon waveguide, silicon nitride, silica, and/or polymer waveguides. In some embodiments, the optical resonator may be a part of any circuit, device and/or arrangement which comprises an optical resonator, such as an interferometer.

In some embodiments, exemplary system 200 may be configured as an interferometer, e.g., a fiber-based Mach-Zehnder interferometer (MZI). For example, optical resonator 202 may be placed in one of the arms of a fiber-based Mach-Zehnder interferometer (MZI), e.g., arm 1 in FIG. 1.

A potential advantage of using fiber-Bragg gratings is in that there is no tradeoff between sensitivity and the effective sensing area, because light at resonance frequencies undergoes strong localization centered on the phase shift, which allows achieving very small sensing lengths. Additionally, in some embodiments, fiber-Bragg gratings can be small in size, immune against electromagnetic interference, and mechanically flexible.

In some embodiments, the fiber-Bragg grating can be fabricated in a polarization-maintaining fiber. In some embodiments, the fiber-Bragg grating can be recoated with acrylic coating after fabrication.

System 200 may further comprise a source laser beam 204, which may be a continuous wave (CW) laser beam source. In some embodiments, source laser beam 204 may be tuned to the maximum transmission notch of optical resonator 202 ($\Delta k=0$). In some embodiments, the source laser beam 204 wavelength may be tuned to a resonant wavelength of the $\pi$-FBG. In some embodiments, for a source laser beam 204 comprising the resonant wavelength, the phase response of the $\pi$-FBG, is linear and/or comprises maximum sensitivity to ultrasound signals.

In some embodiments, source laser beam 204 may be divided into two parts (sample and reference) by beam splitter or fiber optic coupler 210a. In some embodiments, the beam splitter or fiber optic coupler 210a comprises a 50/50 coupler. A first arm denoted 1 in FIG. 2A comprises the sample beam of the interferometer, whereas source laser beam 204 is propagated through optical resonator 202. A second arm denoted 2 in FIG. 2A is the reference beam of the interferometer, wherein the second arm comprises a replica of source laser beam 204 which has not been propagated through optical resonator 204. The propagated sample and reference beams may then be directed to a second splitter/combiner 210b at an output of the resonator, where the two light beams combine and the interference patterns are measured using detector 208.

In some embodiments, the beam splitter or fiber optic coupler 210a divides the power of the optical beam of a CW tunable laser source, for example, an Apex AP3350A.

In some embodiments, system 200 further comprises a balanced photo-detector (BPD) 208, which may have, e.g., a typical common mode rejection ratio (CMRR) of 30 dB and transimpedance gain of 100 kV/A. In some embodiments, the BPD 208 provides high rejection to the intensity fluctuations of the laser source.

In some embodiments, the MZI may further include, e.g., a tunable optical delay line, used to manually control the optical path difference (OPD) between the MZI sample and reference arms 1 and 2, respectively. In some embodiments, the MZI may further include a fiber stretcher and/or a stabilization circuit configured to lock the phases of the MZI arms to quadrature.

FIG. 2B illustrates another exemplary embodiment of a system 220 for ultrasound detection, in accordance with some embodiments. System 220 may have the same or similar components as system 200 in FIG. 2A. However, in some embodiments, system 220 includes interfering the output beam 1 with a reference beam 2 that is a replica of the propagated source laser beam, as propagated through optical resonator 202. In some embodiments, reference beam 2 in FIG. 2B is a time-delayed version of propagated sample beam 1.

Figure 3:
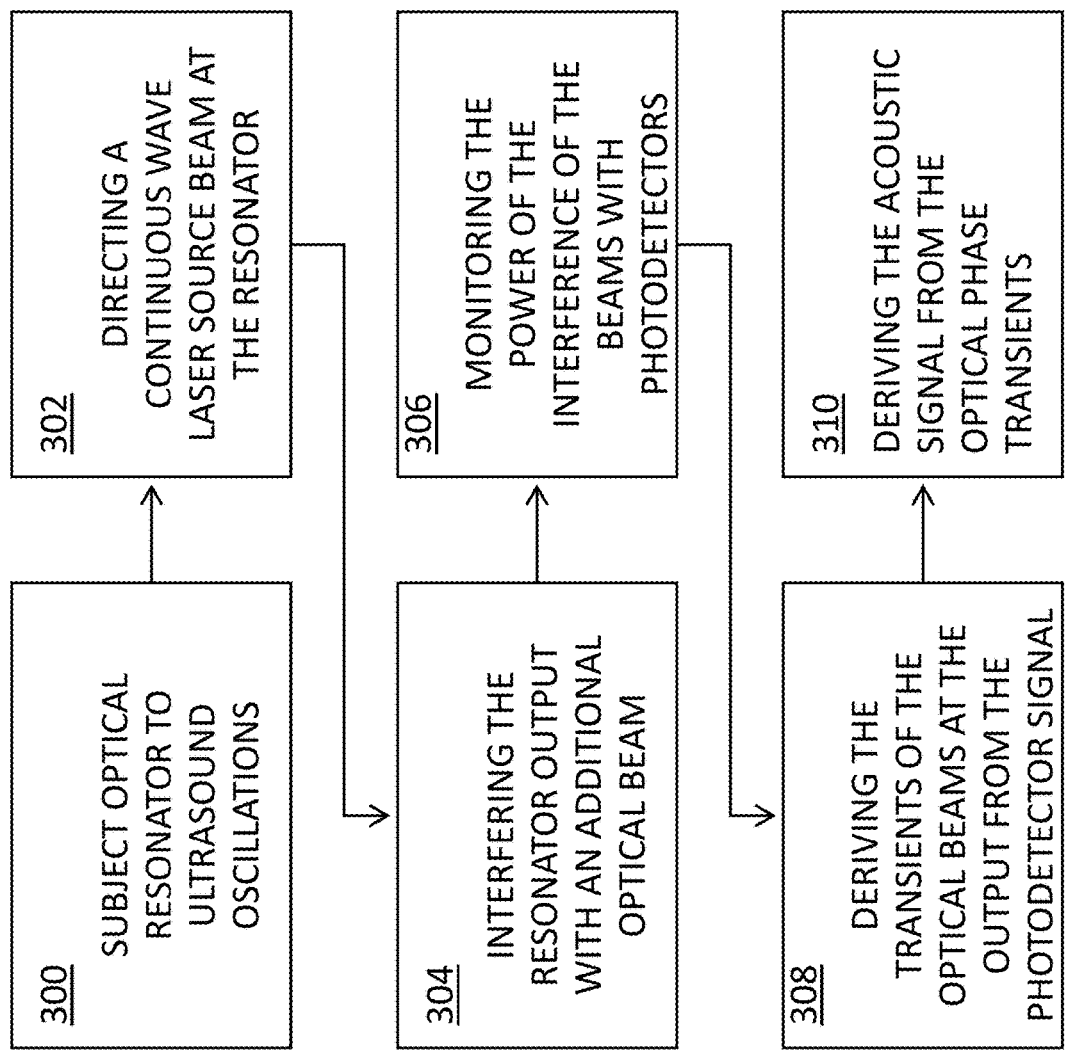
FIG. 3 is a flowchart of the functional steps of a method for ultrasound detection according, to an embodiment.

Exemplary functional steps of a method for ultrasound detection according to the present disclosure, using, e.g., exemplary systems 200, 220, will be described below with reference to the flowchart in FIG. 3.

In some embodiments, at step 300, an optical resonator, such as resonator 202 in FIGS. 2A-2B, may be subjected to an acoustic wave, e.g., ultrasound oscillations by an ultrasound pulse generator 206.

In some embodiments, at step 302, a detection light source, e.g., CW source laser beam 204 in FIGS. 2A-2B, may be directed at optical resonator 202. The output of the CW source laser beam 204 may be described by the following complex field:

$$u_{CW}(t)=\exp[-i(2\pi v_0 t+\varphi_n(t)], \quad (4)$$

where $v_0$ is the laser frequency and $\varphi_n(t)$ represents the phase noise. At a step 304, the detection light source laser beam 204, whose path in marked by 1 in FIGS. 2A-2B, may be interfered with a reference optical beam 2. In some embodiments, the interference may be configured as part of an interferometer, e.g., a fiber-based Mach-Zehnder interferometer (MZI). For example, the light paths 1 and 2 in FIGS. 2A-2B at light coupler 210a may be given by $$u_1(t)=2^{-0.5}u_{CW}(t)$$

and $$u_2(t)=2^{-0.5}iu_{CW}(t),$$

respectively, wherein path 1 represents the sample beam, e.g., in the upper arm of the MZI, and path 2 represents the reference beam, e.g., in the lower arm of the MZI.

The sample path output of optical resonator 202 at sample MZI arm 3 and the reference path 4 may be given by $$u_3(t)=2^{-0.5}\exp[-i(2\pi v_0(t-\Delta T_1+\varphi_n(t-\Delta T_1)+\phi_{US}(t)]$$

$$u_4(t)=2^{-0.5}i\exp[-i(2\pi v_0(t-\Delta T_2+\varphi_n(t-\Delta T_2)] \quad (5)$$

where $\phi_{US}(t)$ is the phase perturbation due to the ultrasound oscillations, and $\Delta T_1$ and $\Delta T_2$ are the delays due to light propagation. In the expression for $u_3(t)$, it may be assumed that laser source 204 is tuned to the center of the resonance notch of resonator 202, where T=1. The delay $\Delta T_1$ represents the propagation time over the fiber of the sample path 1, in accordance with some embodiments, in addition to group delay of the optical resonator 202 at $\Delta k=0$, whereas $\Delta T_2$ includes the propagation delay through the fibers, delay line, and fiber stretcher of the reference path 2 in.

The two path may then be combined by second coupler 210b, wherein the outputs 3 and 4, $u_3(t)$ and $u_4(t)$, are interfered, leading to the following fields:

$$u_5(t)=0.5\exp[-i(2\pi v_0(t-\Delta T_1+\varphi_n(t+\Delta T_1)+\phi_{US}(t)]-0.5\exp[-i(2\pi v_0(t-\Delta T_2+\varphi_n(t-\Delta T_2)],$$

$$u_6(t)=0.5\exp[-i(2\pi v_0(t-\Delta T_1+\varphi_n(t-\Delta T_1)+\phi_{US}(t)]+0.5\exp[-i(2\pi v_0(t-\Delta T_2+\varphi_n(t-\Delta T_2)]. \quad (6)$$

At step 306, the power of the interference may be monitored using, e.g., photodetector 208. Assuming that the MZI is locked to quadrature, i.e. $v_0(T_1-T_2)=N+\frac{1}{4}$, where N is an integer, the power measurement at points 5 and 6 is given by:

$$P_5(t)=0.5\{1+\sin[\phi_{US}(t)+\varphi_n(t-\Delta T_1)-\varphi_n(t-\Delta T_2)]\}$$

$$P_6(t)=0.5\{1-\sin[\phi_{US}(t)+\varphi_n(t-\Delta T_1)-\varphi_n(t-\Delta T_2)]\}. \quad (7)$$

At step 308, the transients of the optical beams at the output from the photodetector signal may be derived. Accordingly, assuming that $\phi_{US}, \varphi_n<<\pi$ during the acoustic measurement, the voltage signal at the output of the balanced photo-detector 208, which is proportional to $P_5(t)-P_6(t)$, is given by $$V(t)=V_0[\phi_{US}(t)+\varphi_n(t-\Delta T_1)-\varphi_n(t-\Delta T_2)]. \quad (8)$$

Because the phase perturbations are small, the phase signal due to ultrasound is given by $\phi_{US}(t)=\delta k_{US}(t)/\alpha$, where $\delta k_{US}(t)$ represents the ultrasound-induced shift of the resonance. Accordingly, the phase noise in the measurement may be theoretically eliminated if the delay between the two MZI arms is identical, i.e. $T_1=T_2$, without affecting the strength of the signal. $\phi_{US}(t)$.

Finally, at step 310, the acoustic signal may be derived from the optical phase transients measured at step 308.

In some embodiments, the method comprises balancing out the arms of the interferometer. In some embodiments, balancing the arms of the interferometer compensates for the interferometric phase-to-intensity noise contribution. In some embodiments, phase variations produced by mechanical or thermal fluctuations can be cancelled by the stabilization system.

In some embodiments, the exemplary system as depicted by FIGS. 2A-2B comprises a flat acoustic PZT transducer. In some embodiments, the system comprises a pulse generator. In some embodiments, the PZT transducer and the pulse generator are coupled such that squarewave ultrasound pulses are produced. In some embodiments, the pulses comprise a duration of 10 us.

In some embodiments, the method comprises producing two interferometric signals, in counter-phase, that are detected by the BPD 208. In some embodiments, the output of the BPD 208 comprises a voltage signal proportional to the difference of the detected interferograms:

$$V_0(t) = V_0 \cos[\Delta\phi(t) + \delta(t)] + n(t)$$

wherein in the equation above, $V_0$ is the voltage amplitude, which is proportional to the fringe contrast, $\Delta\phi(t)$ contains the information about the ultrasound signal to be recovered, $\delta(t)$ includes any random phase fluctuations between the arms of the interferometer, and $n(t)$ is the voltage noise from the electronics.

In some embodiments, and in order to maximize the sensitivity of the interferometer, a proportional-integral stabilization circuit drives a piezoelectric fiber-stretcher, locking and stabilizing $\delta(t)$ to a constant value of $\pi/2$. In some embodiments, the stabilization and locking system comprises a bandwidth of 3 kHz, which enables compensation for temperature variations and low-frequency mechanical vibrations. Under these conditions, and at weak acoustic perturbations, the output signal from the detector changes linearly with $\Delta\phi(t)$. Finally, in some embodiments, $V_0(t)$ is monitored by an oscilloscope and processed by a computer.

In some embodiments, method allows the decoupling between the laser phase and intensity noise. In some embodiments, if the laser is tuned at the resonance of the grating, phase-noise do not produce intensity fluctuations of the transmitted field. Therefore, in some embodiments, laser phase-noise are converted into intensity noise due to the interference with the reference field. Consequently, the dominant processes determining the noise in the method are the relative intensity noise (RIN) and the conversion of phase noise into intensity noise. In some embodiments, the contribution of the phase noise can be greatly reduced by matching the OPD between the arms of the interferometer. In some embodiments, the contribution can be reduced due to an improvement of the SNR caused by the minimization of the phase-to-intensity noise conversion and the maximization of the contrast of the interferometric signal.

EXPERIMENTAL RESULTS

Figure 4A:
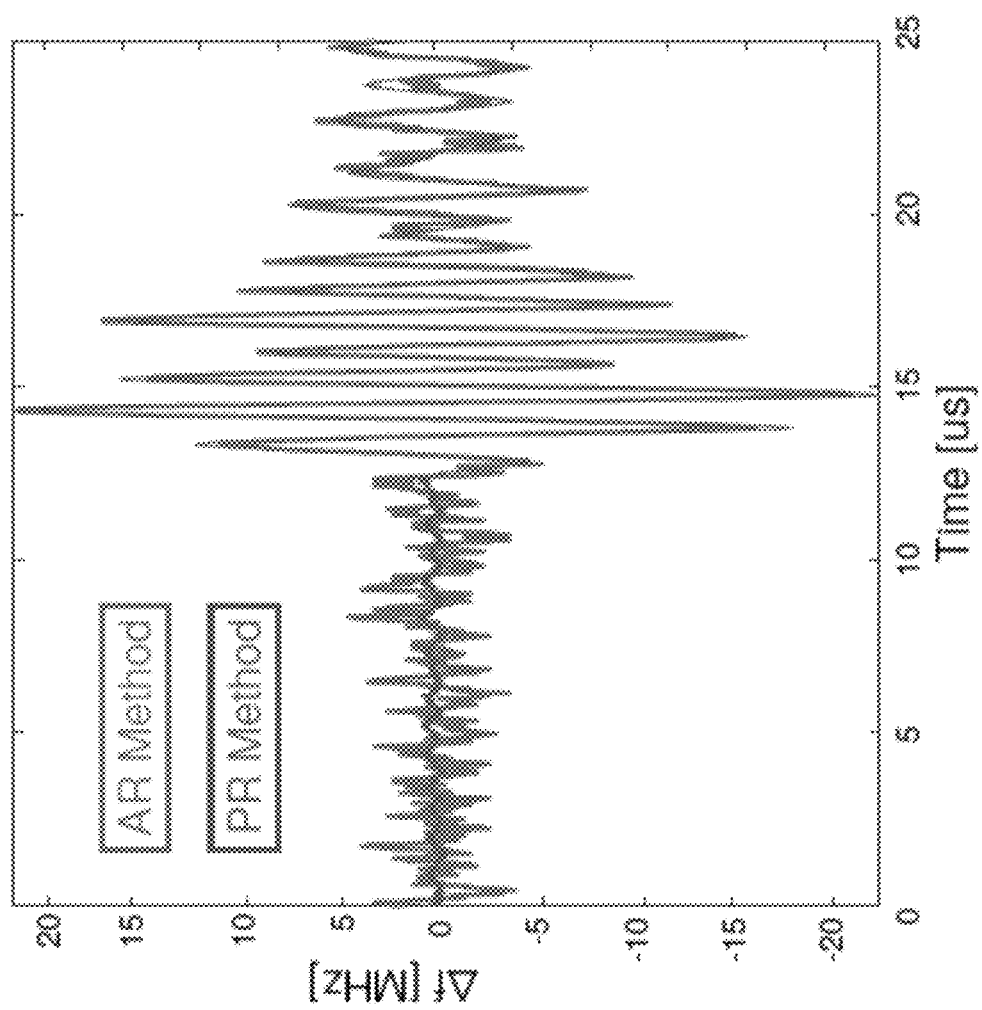
FIGS. 4A-4C illustrate experimental results.
Figure 4B:
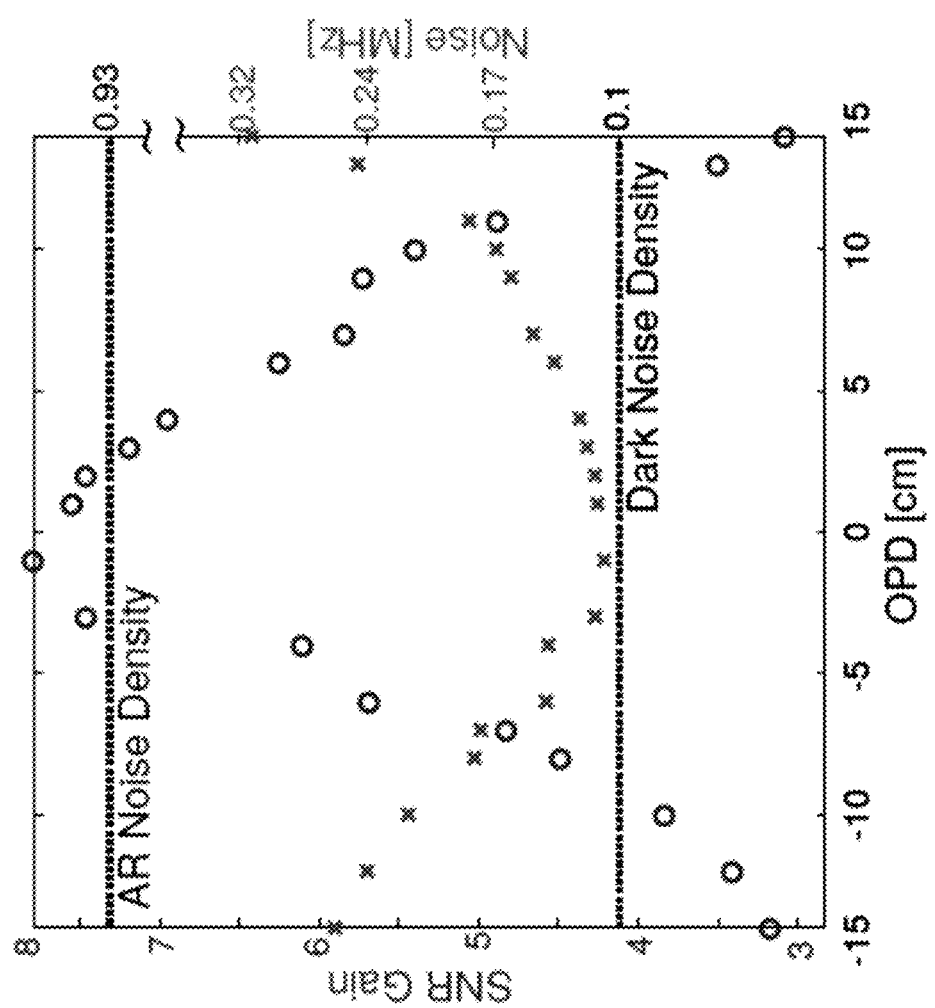
Figure 4C:
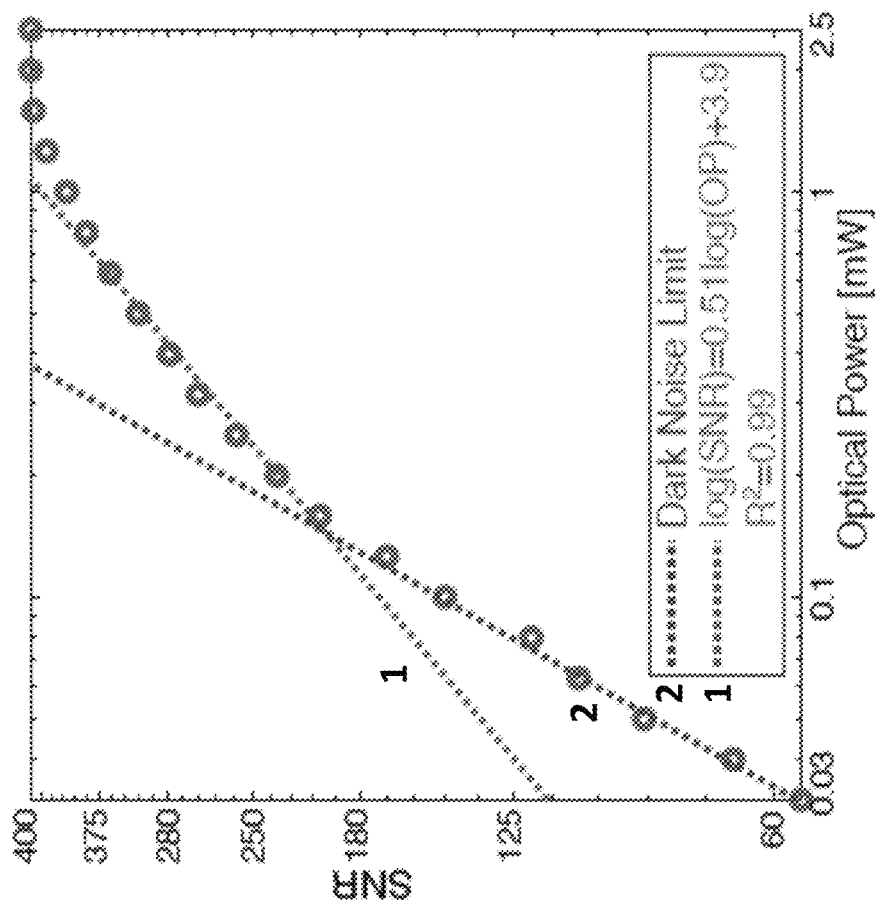

FIGS. 4A-C illustrate experimental results using the present method and an intensity-based technique, e.g., techniques comprising a linear amplitude response. In the intensity measurements, the laser source was tuned to the maximum slope of the resonator, whereas in present method, the OPD was set to zero ($T_1 = T_2$) for maximum SNR.

The laser power was 0.1 mW in both cases, which was selected so as not to saturate the photodetector. As can be seen in FIG. 4, the two signals are almost identical, whereas the SNR obtained with present method is 8 times lower.

To evaluate the effect of the OPD on the SNR of the present method, the measurement was repeated for different values of OPDs over a span of 30 cm. The noise is determined by calculating the standard deviation of the signal before the arrival of the ultrasound pulse ($t < 10$ μs in FIG. 4) over a bandwidth of 4 MHz (i.e., the bandwidth of the photodetector).

The output noise density of the present method as a function of the OPD is shown in FIG. 4B, as expressed both in terms of noise and SNR gain in comparison to intensity-based measurements. FIG. 4B also shows the noise density of the electronics (dark-current noise). As expected, when the magnitude of the OPD is increased, the noise cancellation obtained with the present method diminishes. Additionally, it is noted that when the OPD was set to zero, the noise in this measurement was due to the dark current of the photo-detector.

In the final measurement, the SNR of the present method was tested for a zero OPD at different power levels. Since the trans-impedance amplifier in the balanced photo-detector amplifies the differential signal from the two photodiodes, rather than each individual signal, each photo-diode may be illuminated with powers higher than 0.1 mW without leading to signal saturation.

FIG. 4C shows the SNR gain of the present method for different power levels with respect to the maximum SNR of intensity-based measurements for the same acoustic signal, which was reached at a power of approximately 10 μW. The figure is presented as a log-log plot and reveals three regimes of SNR. For powers up to approximately 0.1 mW, the SNR grows linearly with the power, i.e. a slope of approximately 1 in the log-log plot, indicating that the main noise source is from the dark current of the photo-detector. For powers between approximately 0.1 mW and 1 mW, the slope of the curve is approximately half, indicating shot-noise limited detection in which the SNR grows as the square root of the power. Finally, for powers above 1 mW, the SNR gains diminished further, reaching full saturation at 2 mW.

In some embodiments, the present method more robust than the intensity-based technique due to at least one of the laser phase noise compensation and the balanced photodetection, which provides a significant enhancement of the SNR without a significant added complexity to the system. Additionally, in some embodiments, the present method can be adapted to schemes with high dynamic range and multiplexing capabilities, such as pulse interferometry.

What is claimed is:

1. A system for detecting acoustic waves, said system comprising:
    an optical resonator configured to be impinged by acoustic waves;
    a continuous-wave source laser beam directed to said optical resonator, wherein said source laser beam is propagated through said optical resonator, thereby generating a propagated laser beam; and
    an interferometer configured for detecting said acoustic waves by monitoring transients in an optical phase in said propagated laser beam, wherein said transients are indicative of a waveform of said acoustic waves, wherein said monitoring comprises interfering said propagated laser beam with a reference beam,
    wherein said propagated laser beam and said reference laser beam have a matched optical path difference at a wavelength of said source laser beam.

2. The system of claim 1, wherein said reference beam comprises a replica of said source laser beam.

3. The system of claim 1, wherein said reference beam comprises a time-delayed version of said propagated laser beam.

4. The system of claim 1, wherein said optical resonator is selected from the group consisting of: π phase-shifted Bragg grating (π-BG), Fabry-Perot cavity, and optical-ring resonator.

5. The system of claim 1, wherein said laser beam is tuned to a center of a transmission notch of said optical resonator.

6. The system of claim 1, wherein said interferometer is a Mach-Zehnder interferometer (MZI).

7. The system of claim 1, wherein said monitoring further comprises measuring, by at least one balanced photo-detector, an optical power transmission in said propagated laser beam and said reference laser beam, wherein said optical power transmission is indicative of said transients.

8. The system of claim 1, wherein said acoustic waves are ultrasound acoustic waves, and wherein said ultrasound acoustic waves are generated opto-acoustically via a transformation of a modulated optical beam into acoustic waves.

9. The system of claim 8, wherein the modulated optical beam consists of optical pulses.

10. A method of detecting acoustic waves, the method comprising:
    directing a continuous-wave source laser beam to an optical resonator that is impinged by acoustic waves, wherein said source laser beam is propagated through said optical resonator, thereby generating a propagated laser beam; and
    detecting said acoustic waves by monitoring, using an interferometer, transients in an optical phase in said propagated laser beam, wherein said transients are indicative of a waveform of said acoustic waves, wherein said monitoring comprises interfering said propagated laser beam with a reference beam, and wherein said propagated laser beam and said reference laser beam have an optical path difference equal to zero at a wavelength of said source laser beam.

11. The method of claim 10, wherein said reference beam comprises a replica of said source laser beam.

12. The method of claim 10 and wherein said reference beam comprises a time-delayed version of said propagated laser beam.

13. The method of claim 10, wherein said laser beam is tuned to a center of a transmission notch of said optical resonator.

14. The method of claim 10, wherein said monitoring further comprises measuring an optical power transmission in said propagated laser beam and said reference laser beam, wherein said optical power transmission is indicative of said transients.

15. The method of claim 10, wherein said acoustic waves are ultrasound acoustic waves.

16. The method of claim 15, wherein said ultrasound acoustic waves are generated opto-acoustically via a transformation of a modulated optical beam into acoustic waves, and wherein said modulated optical beam comprises optical pulses.

17. The system of claim 6, wherein the MZI further comprises a tunable optical delay line, configured to control the OPD between sample and reference arms of the MZI.

18. The system of claim 6, wherein the MZI further comprises at least one of a fiber stretcher and a stabilization circuit, configured to lock phases of arms of the MZI to quadrature.

19. A system for detecting acoustic waves, said system comprising:
    an optical resonator configured to be impinged by acoustic waves;
    a continuous-wave source laser beam directed to said optical resonator, wherein said source laser beam is propagated through said optical resonator, thereby generating a propagated laser beam; and
    an interferometer configured for detecting said acoustic waves by monitoring transients in an optical phase in said propagated laser beam, wherein said transients are indicative of a waveform of said acoustic waves, wherein said monitoring comprises interfering said propagated laser beam with a reference beam,
    wherein said acoustic waves are ultrasound acoustic waves, and wherein said ultrasound acoustic waves are generated opto-acoustically via the transformation of a modulated optical beam into acoustic waves.

* * * * *